United States Patent [19]

Gibbons et al.

[11] 4,311,358

[45] Jan. 19, 1982

[54] ILLUMINATION DEVICE FOR FLUORESCENCE MICROSCOPES

[75] Inventors: Gregory C. Gibbons, Virum; Lars Munck, Helsingor, both of Denmark

[73] Assignee: De Forenede Bryggerier A/S, Denmark

[21] Appl. No.: 88,320

[22] Filed: Oct. 25, 1979

[30] Foreign Application Priority Data

Nov. 1, 1978 [SE] Sweden .............................. 7811307
May 10, 1979 [SE] Sweden .............................. 7904091

[51] Int. Cl.³ ............................................. G02B 21/16
[52] U.S. Cl. .................................................... 350/91
[58] Field of Search ........................................ 350/91

[56] References Cited

FOREIGN PATENT DOCUMENTS 2348567 4/1975 Fed. Rep. of Germany ........ 350/91

OTHER PUBLICATIONS

Zeidler, "The Fluorescence Microscope", Laboratory Equipment Digest, vol. 12, No. 7, pp. 48, 50-54, 56, 57, Jul. 1974.

Primary Examiner—John K. Corbin
Assistant Examiner—Matthew W. Koren
Attorney, Agent, or Firm—Beveridge, De Grandi, Kline & Lunsford

[57] ABSTRACT

An illumination device permitting microscopes, for use of the microscope as a fluorescence microscope, comprises a light-screening tube (2, 4) preferably of variable length, one end of the tube being connectible to the microscope objective and the other end being disposed to surround the sample which is intended for microscopic observation on the sample stage (1) of the microscope. An opening in the tube is arranged to direct high intensity UV and/or visible light towards the sample. In that the light is directed towards the sample bypassing the optics of the microscope, substantially unchanged light intensity will be realized from the light source to the sample, which considerably facilitates fluorescence studies with, in particular, microscope objectives of low magnifying power and low numerical aperture.

9 Claims, 1 Drawing Figure

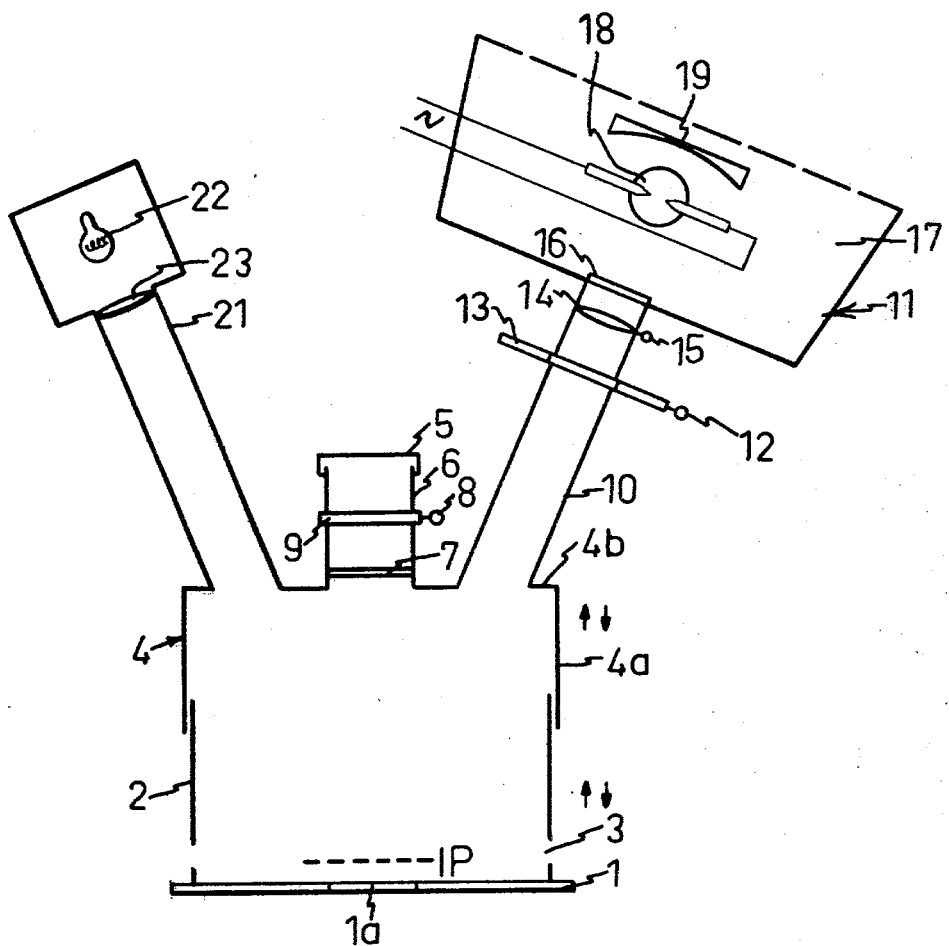

ILLUMINATION DEVICE FOR FLUORESCENCE MICROSCOPES

The present invention relates to an illumination device for a microscope, permitting use thereof as a fluorescence microscope with incident light.

In prior art fluorescence microscopes, the light source is disposed to direct light towards a semi-transparent mirror or prism device arranged between the objective and the ocular lenses, the device directing the received light towards the sample through the objective. Since the light must in this manner traverse several light-absorbing optical parts before reaching the sample which it is to excite to fluorescence, the light intensity on the sample is but a fraction of the original light intensity transmitted from the source. In particular in weakly-magnifying microscopes, this factor causes trouble, since such microscopes have a low numerical aperture, poor light passing power (the total light passing power of the microscope being even smaller since the objective, in accordance with the above, also acts as a condensor), and slight image brightness, such that the already weak emission radiation from the sample cannot be used for acceptable image reproduction of the sample to the naked eye, or to other measurement devices such as a photocell or video tube.

The object of the present invention is to provide an illumination device which does not possess this inconvenience. This is achieved according to the invention with the device which has the characteristics disclosed in the claims.

According to the invention, the light is, thus, directed, not through the microscope objective, but is directly concentrated onto the sample, whereby the radiation intensity emitted from the light source impinges substantially unreduced on the sample. In this instance, UV light of short wavelengths (less than about 360 nm) can excite light from the sample, which, with normal glass objectives, is impossible, since the glass in such objectives greatly absorbs light of less than about 370 nm. Consequently, microscopes with a low magnifying power, from about 1,5X to 10X, may be effectively utilised for fluorescence examination. Moreover, the invention makes possible in as advantageous a manner the observation and examination of larger samples ("macromicroscopy") than is possible with highly-magnifying microscope objectives.

Furthermore, the invention ensures that the human eye is not exposed to injurious UV light and that the sample is not illuminated with ambient light, and hence the contrast in the observed sample is greater.

The invention may advantageously be used for fluorescence microscope studies within fields such as microbiology, mineralogy, botany, coal-petrography, and the technologies of foodstuffs, crushing and milling, textiles, paper, laundering and medicine.

An embodiment of the device according to the invention will be described in greater detail hereinbelow with reference to the accompanying drawing which schematically illustrates the embodiment under discussion.

The illustrated embodiment is connected to a standard stereomicroscope.

Of the standard microscope, which has a movable objective and movable sample stage, only the movable sample stage 1 is shown, which has a glass window 1a in its center and which, according to the invention, supports a light-screening tubular portion 2 which surrounds a dark chamber in which is located the field of view which may be observed from the ocular of the microscope. The tubular portion 2 may be fixedly mounted on the stage 1, in which event it has an opening 3 for insertion and manipulation of the sample which is to be observed in the observation field of the microscope and for removal of the sample from the observation field. A second light-screening tubular portion 4 is telescopically shiftably passed over the tubular portion 2, this second tubular portion being, at its upper end, fixedly mountable in light-tight relationship on the objective of the microscope by means of a coupling piece 5. Alternatively, it may be mounted on the housing supporting the objective, for example by means of a screw thread. An upper portion 6 of smaller diameter on the tube portion 4 contains a UV light-absorbing filter 7 which also serves as a dust protector and is of the type designated, for example KV 418. Furthermore, in this upper portion 6, there is mounted a holder 8 for one or more emission filters 9, which holder may be of the revolver type or sliding type, such that a desired wavelength or desired wavelength band may be directed to the microscope ocular from that emission spectrum which is emitted by the sample after illumination from a light source which will be described below.

In the shoulder 4 b formed between the upper portion 6 of the tubular portion 4 and its lower portion 4 a, there is an opening to which one end of a light-screening tube 10 is fixedly mounted in light-tight relationship, the other end of the tube being connected, substantially light-tight, to, and supporting, a source 11 for high intensity light. A sliding holder 12 is desposed in the tube 10 for excitation filters 13 such that a desired excitation filter may be interposed in the path of the light from the light source, for illuminating the sample with a desired excitation wavelength or wavelength band. Furthermore, the tube contains, in sequence above the excitation filter holder, a UV light-permeable collector 14 which, in a known manner, is shiftable in the axial direction of the tube 10 by shifting of an operating arm 15 fixedly mounted thereon in a helical groove in the tube 10, for optimal adjustment (depending on the objective and ocular) of received light on the plane of focus of the microscope, which is shown on the drawing by means of a broken line IP, and a UV light-permeable heat filter 16. The light source consists of a housing 17, a high intensity UV lamp 18, for example a mercury arc lamp, and, finally, a concave mirror 19 over the lamp 18, the mirror directing the light into the tube 10.

There is preferably provided a further opening in the abovementioned shoulder 4 b, to which opening is connected in light-tight relationship one end of a further tube 21, whose other, upper end is connected to a source 22 for incandescent light, and which is disposed to direct light emitted from this source onto the sample, this light being condensed, by means of a fixed condensor 23 in the tube 21, to the above-mentioned plane of focus IP.

It should well be apparent from the above that the stage 1 may be optionally raised or lowered, as shown by means of arrows in the tubular portion 2, for bringing samples of different heights into the plane of focus IP, while still protecting the observer from injurious UV radiation by means of the UV light screening device formed by the tube 10 and the telescopically-mounted tubular portions 2 and 4. Moreover, the optimal adjustment and centering of the UV light, and possibly incandescent light, on the plane of focus IP will also be retained irrespective of the height of the sample. In the same manner, the objective or microscope tube may be raised or lowered integrally with the tubular portion 4 fixed thereon and the light sources 22 and 11 fixed hereon, as shown by means of arrows at the tubular portion 4, for shifting the plane of observation. In this instance, the adjustment of the UV light is retained on the plane of observation of the sample while UV light is screened off from the observer by means of the screening off device 10, 2 and 4.

The inventive principle as described above is, naturally, also applicable in association with microscopes with fixed sample stages and movable optics, and in association with immovable optics and movable stages. The microscope may be provided with fixed or interchangeable objectives, revolving objectives or zoom objectives and may, naturally, advantageously be provided with a source of incandescent light or source of high intensity light for transmitted light through the window 1a. It will be furthermore appreciated that the telescopic tube portions may be replaced by, for example a bellows device. Alternatively, the emission filter 9 may advantageously be disposed higher up in the emission radiation path from the sample, for example, at the microscope ocular.

We claim:

1. An illumination device for a miroscope, permitting use of the microscope as a fluorescence microscope, said device comprising:
    a first tube member having a first end adapted for light-tight connection to a microscope objective, a second end adapted for attachment to the stage of the microscope to enclose a sample thereon, and a light-screening wall portion joining said first tube member first end and second end and having therein means permitting introduction of a sample onto the stage, one of the first tube member first end and wall portion having at a distance to one side of said light-tight connection a first opening;
    a second tube member having a first end coupled to said first opening, a second end, and a light-tight wall portion joining said second tube member first end and second end; and
    a light source connected to said second tube member second end for directing light therefrom through said second tube member and said first opening towards said first tube member second end to illuminate the stage of the microscope and any sample thereon.

2. An illumination device as claimed in claim 1 in which said first tube member is capable of longitudinal extension and retraction.

3. An illumination device as claimed in claim 2 in which said first tube member telescopes.

4. An illumination device as claimed in claim 1, 2, or 3 in which said light source is a high intensity light source and in which said device further comprises a lens between said light source and the stage for concentrating light from said light source onto a sample on the stage.

5. An illumination device as claimed in claim 1, 2, or 3 in which said light source is a high intensity ultraviolet light source.

6. An illumination device as claimed in claim 5 further comprising a lens between said ultraviolet light source and the stage for concentrating light from said ultraviolet light source onto a sample on the stage.

7. An illumination device as claimed in claim 1 further comprising an emission filter in said first tube member.

8. An illumination device as claimed in claim 1 further comprising an excitation filter in said second tube member.

9. An illumination device as claimed in claim 1 in which one of the first tube member first end and wall portion has at a distance to one side of said light-tight opening a second opening and in which said device further comprises a source of incondescent light coupled to said second opening for directing light therefrom through said second opening towards said first tube member second end to illuminate the stage of the microscope and any sample thereon.

* * * * *